US007282618B2

(12) United States Patent
Milstein et al.

(10) Patent No.: US 7,282,618 B2
(45) Date of Patent: Oct. 16, 2007

(54) METHOD FOR THE PRODUCTION OF ARYL ALKENES

(75) Inventors: David Milstein, Rehovot (IL); Haim Weissman, Lod (IL); Xiao-Ping Song, Lawrence, KS (US)

(73) Assignee: Yeda Research and Development Co., Ltd., Rehovot (IL)

( * ) Notice: Subject to any disclaimer, the term of this patent is extended or adjusted under 35 U.S.C. 154(b) by 664 days.

(21) Appl. No.: 10/450,379

(22) PCT Filed: Dec. 13, 2001

(86) PCT No.: PCT/US01/47570

§ 371 (c)(1),
(2), (4) Date: Dec. 2, 2003

(87) PCT Pub. No.: WO02/055455

PCT Pub. Date: Jul. 18, 2002

(65) Prior Publication Data

US 2004/0073075 A1  Apr. 15, 2004

(30) Foreign Application Priority Data

Dec. 13, 2000  (IL) ..................................... 140275

(51) Int. Cl.
*C07C 2/68* (2006.01)
(52) U.S. Cl. ..................................................... 585/467
(58) Field of Classification Search ................ 585/454, 585/467, 469, 435, 436, 438
See application file for complete search history.

(56) References Cited

U.S. PATENT DOCUMENTS 3,674,884 A  7/1972  Moritani et al.
3,855,329 A  12/1974  Shue
6,127,590 A  10/2000  Taube et al.
2001/0037044 A1  11/2001  Matsumoto et al.

FOREIGN PATENT DOCUMENTS

JP       1193241       8/1989

OTHER PUBLICATIONS

Asano, et al., "Aromatic Substitution of Olefins. The Reaction of Ferrocene with Styrene in the Presence of Palladium Acetate", Chemical Communications. 1970, 1293.
Dichmann, et al., "The 2:1 Vanadyl Acetylacetonate:1,4-Dioxan Complex. A Nuclear Magnetic Resonance and X-Ray Crystal Structure Study" Chemical Communications. 1970,1295.
Fujiwara, et al., "Aromatic Substitution of Olefins. VI. Arylation of Olefins with Palladium (II) Acetate", Journal of the American Chemical Society. Dec. 3, 1969, Vol. 91, No. 25, 7166-7169.
Fujiwara, et al., "Aromatic Substitution of Olefins. 25. Reactivity of Benzene, Naphthalene, Ferrocene, and Furan toward Styrene, and the Substituent Effect on the Reaction of Monosubstituted Benzenes with Styrene", Journal of Organic Chemistry. 1976, vol. 41, No. 10, 1681-1683.
Fujiwara, et al., "Exploitation of Synthetic Reactions via C-H Bond Activation by Transition Metal Catalysts. Carboxylation and Aminomethylation of Alkanes or Arenes", SYNLETT. Jul. 1996, 591-600.
Hong, et al., "Rhodium Carbonyl-Catalyzed Activation of Carbon-Hydrogen Bonds for Application in Organic Synthesis. V*. Phenylation of Olefins with Benzenes", Journal of Molecular Catalysis. 1984, vol. 26, 297-311.
Jia, et al., "Efficient Activation of Aromatic C-H Bonds for Addition to C-C Multiple Bonds", Science. Mar. 17, 2000, vol. 287, 1992-1995.
Jia, et al., "Novel Pd(II)- and Pt(II)-Catalyzed Regio-and Stereoselective trans-Hydroarylation of Alkynes by Simple Arenes", Journal of American Chemical Society. 2000, vol. 122, 7252-7263.
Kakiuchi, et al., "Ruthenium-Catalyzed Addition of Aromatic Imines at the ortho C-H Bond to Olefins", Chemistry Letters. 1996, 111-112.
Matsumoto, et al., "Anti-Markovnikov Olefin Arylation Catalyized by an Iridium Complex", Journal of American Chemical Society. 2000, vol. 122, 7414-7415.
Matsumoto, et al., "Oxidative Arylation of Ethylene with Benzene to Produce Styrene", Chemistry Letters. 2000, 1064-1065.
Mikami, et al., "Catalytic C-H Bond Activation-Asymmetric Olefin Coupling Reaction: The First Example of Asymmetric Fujiwara-Moritani Reaction Catalyzed by Chiral Palladium (II) Complexes", Chemistry Letters. 1999, 55-56.
Miura, et al, "Palladium-Catalyzed Oxidative Cross-Coupling of 2-Phenylphenols with Alkenes", Chemistry Letters. 1997, 1103-1104.
Miura, et al, "Oxidative Cross-Coupling of N-(2' -Phenylphenyl) benzene-sulfonamides or Benzoic and Naphthoic Acids with Alkenes Using a Palladium-Copper Catalyst System under Air", Journal of Organic Chemistry. 1998, vol. 63, 5211-5215.
Moritani, et al., "Aromatic Substitution of Styrene-Palladium Choride Complex", Tetrahedron Letters. 1967, No. 12, 1119-1122.
Murai, et al., "Efficient Catalytic Addition of Aromatic Carbon-Hydrogen Bonds to Olefins", Nature. Dec. 9, 1993, vol. 366, 529-531.
Sasaki, et al., "C=C Double Bond Insertion in Catalytic C-H Activation. Dehydrogenative Cross Coupling of Arenes with Olefins", Chemistry Letters. 1988, 685-688.
Shue, Robert, "Reactions of Aromatics and Olefins Catalyzed by Homogeneous Palladium (II) Compounds Under Oxygen", Journal of Catalysis. 1972, vol. 26, 112-117.
Schultz, et al., "The Role of Sulphenate Esters in Sulphoxide Photoracemization", Chemical Communications. 1970, 1294.
Tsuji, et al., "Palladium-Catalyzed Oxidative Coupling of Aromatic Compounds with Olefins Using t-Butyl Perbenzoate as a Hydrogen Acceptor", Tetrahedron. 1984. vol. 40, No. 14, 2699-2702.

*Primary Examiner*—Thuan Dinh Dang
(74) *Attorney, Agent, or Firm*—Browdy and Neimark, PLLC

(57) ABSTRACT

The present invention relates to a novel oxidative coupling arenes with olefins to yield aryl alkenes, which uses ruthenium (Ru) or Osmium (Os) compounds as catalysts.

25 Claims, No Drawings

METHOD FOR THE PRODUCTION OF ARYL ALKENES

FIELD OF THE INVENTION

The present invention relates to a novel oxidative coupling of arenes with olefins to yield aryl alkenes, which uses ruthenium (Ru) or osmium (Os) compounds as catalysts.

BACKGROUND OF THE INVENTION

Catalytic carbon-carbon bond formation by C—H activation is a topic of much current interest. Significant progress has been made in recent years in the development of synthetically useful catalytic addition of arenes to alkenes to give the saturated alkyl arenes (Murai et al, 1993; Kakiuchi et al, 1996; Jia et al, 2000a, 2000b; Matsumoto et al, 2000a).

Catalytic oxidative coupling of arenes with alkenes to give aryl alkenes, in which the double bond is preserved, is a highly desirable goal. Such a reaction, which does not require the utilization of a reactive substituent, and does not produce waste, may have an advantage over other methods for the preparation of aromatic alkenes, such as the well-known Heck reaction for the vinylation of aryl halides. Stoichiometric coupling of olefins with arenes promoted by Pd(II) is well known (Moritani et al, 1967; U.S. Pat. No. 3,674,884, 1972).

Tsuji et al (1984) and lately Fujiwara et al (1996) and Mikami et al (1999) have demonstrated catalysis by utilizing peroxides as oxidants in their systems. While good catalytic activity was achieved with some alkenes, acrylates resulted in low activity (~10 turnovers). The use of peroxide oxidants and acetic acid solvent in these systems is problematic from the industrial point of view. Attempts to use $O_2$ or air resulted in low activity in intramolecular (Miura et al, 1997, 1998) and intermolecular (Fujiwara et al, 1969, 1976; Asano et al, 1970; Shue, 1972; U.S. Pat. No. 3,855,329) coupling and alkene oxidation took place in the intermolecular reaction.

Another approach utilizing Rh carbonyl clusters under high (20-30 atm) CO pressure (Hong et al, 1984) resulted in modest catalytic activity with concomitant hydrocarbonylation of the alkene. Low catalytic activity was reported for the Rh-catalyzed photochemical coupling of arenes with alkenes, in which concomitant hydrogenation of the alkene took place and biaryls were formed as by-products (Sasaki et al, 1988; JP 1193241). A very low yield Rh catalyzed oxidative phenylation of ethylene to styrene was reported (Matsumoto et al, 2000b; U.S. Pat. No. 6,127,590).

SUMMARY OF THE INVENTION

It has now been found according to the present invention that aryl alkenes can be produced by reaction of arenes with olefins in the presence of ruthenium (Ru) or osmium (Os) compounds as catalysts. The reaction can be carried out in the presence of molecular oxygen as the oxidant or in the absence of $O_2$, in which case the alkene itself serves as the oxidant. Reasonable turnover numbers were achieved.

The present invention thus relates to a method for the production of an aryl alkene comprising reacting an arene with an olefin in the presence of a Ru or Os compound as catalyst. An advantage of the process of the present invention using Ru or Os catalysts is the absence of the necessity of an acid solvent or a peroxide. Furthermore, compared to the prior art process using Rh catalysts and CO, much lower pressure of CO may be used.

In one embodiment, the reaction is carried out in the presence of molecular oxygen. The addition of a catalytic amount of hydroquinone or of a quinone such as, but not being limited to, benzoquinone, improves the yield of the reaction. The reaction may be carried out in an inert atmosphere but it is preferably carried out in an atmosphere containing CO. CO pressures are between 0 to about 100 atm, preferably between 1 to 10 and most preferably between 6 to 8 atm.

While it is expected that any ruthenium or osmium compound could be used in accordance with the present invention, preferred examples of ruthenium compounds that may be used include, but are not limited to, $RuCl_3 \cdot 3H_2O$, $[Ru(CO)_3Cl_2]_2$, $[(\eta^6\text{-}C_6H_6)RuCl_2]_2$, $[(\eta^6\text{-}C_6H_6\text{—}Ru(H_2O)_3](F_3CSO_3)_2$, $Ru(NO)Cl_3 \cdot 5H_2O$, $Ru(F_3CCOCHCOCF_3)_3$ and $Ru_3(CO)_{12}$. In one preferred embodiment, the ruthenium compound is $RuCl_3 \cdot 3H_2O$.

Preferred examples of osmium compounds that may be used according to the invention include, but are not limited to, $OsCl_3 \cdot 3H_2O$, $OsO_4$, $[Os(CO)_3Cl_2]_2$, $[(\eta^6\text{-}C_6H_6)OsCl_2]_2$, $Os(NO)Cl_3 \cdot 5H_2O$, $Os(F_3CCOCHCOCF_3)_3$ and $Os_3(CO)_{12}$.

Most of the Ru and Os compounds present a higher catalytic activity in a CO atmosphere but the compounds $Ru(F_3CCOCHCOCF_3)_3$, $Ru_3(CO)_{12}$ and $Os_3(CO)_{12}$ exhibit catalytic activity in the absence of a CO atmosphere.

In one embodiment, the method of the invention is used for the production of an aryl alkene of the formula:

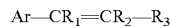

wherein Ar is an aryl radical and $R_1$, $R_2$, $R_3$ independently of each other represent H, alkyl, aryl, alkoxycarbonyl or aryloxycarbonyl.

As used herein, the term "aryl" includes carboaryl radicals such as, but not being limited to, phenyl and naphthyl, and heteroaryl radicals such as, but not being limited to, furyl, thienyl, the aryl radical being optionally substituted by one or more halogen atoms, alkyl optionally substituted by one or more halogen atoms or alkoxy, and the term "arene" relates to the aromatic compound from which the aryl radical is derived, e.g., benzene, naphthalene furan, thiophene, that may be substituted as indicated for the aryl radical.

As used herein, the term "alkyl" for an alkyl radical itself or part of an alkoxy radical includes straight and branched radicals having up to 25 carbon atoms, preferably up to 20, more preferably up to 10, and most preferably up to 6 carbon atoms such as methyl, ethyl, propyl, butyl, pentyl and hexyl, wherein said alkyl may be optionally substituted by halogen such as fluoro, chloro and bromo, or by alkoxy.

In one embodiment, the aromatic compound may be substituted by one or more alkyl or fluoroalkyl, preferably methyl or $CF_3$, radicals, and may be, for example, toluene or xylene. In another embodiment, the aromatic compound may be substituted by an alkoxy, preferably methoxy, radical, and may be, for example, anisole or 2-methoxynaphthalene. In a further embodiment, the aromatic compound may be substituted by a halogen such as fluoro, chloro and bromo, and may be, for example, chlorobenzene.

When $R_1$, $R_2$, $R_3$ are hydrogen the reaction is carried out with ethylene. Thus when the arene is benzene the end product is styrene and when the arene is naphthalene the end product is vinylnaphthalene. When $R_1$, $R_2$, $R_3$ are alkyls, the end product will be an alkenyl arene. $R_1$, $R_2$, $R_3$ may also be alkyl substituted by one or more halogen atoms such as chloro, bromo, and preferably fluor. In one example as shown herein benzene is reacted with 3,3,4,4,5,5,6,6-nonafluorohex-1-ene thus producing (3,3,4,4,5,5,6,6-nonafluorohex-1-enyl)benzene.

In one preferred embodiment of the invention $R_1$ is an alkoxycarbonyl radical such as ethoxycarbonyl and, more preferably, methoxycarbonyl and $R_2$, $R_3$ are hydrogen. Thus for the preparation of an alkyl cinnamate, benzene is reacted with an alkyl acrylate such as methyl or ethyl acrylate. When a substituted benzene or naphthalene compound is reacted with an alkyl acrylate, the corresponding alkyl 2-propanoate derivatives are obtained such as methyl 3-(chlorophenyl)-2propanoate, methyl 3-methoxyphenyl-2-propanoate, methyl 3tolyl-2-propanoate, methyl 3-(2,5-dimethylphenyl)-2-propanoate, methyl 3-(2-naphthyl)-2-propanoate and methyl 3-(2- or 6- or 7-methoxy-2-naphthyl)-2-propanoate, that are produced by reacting an arene selected from chlorobenzene, anisole, toluene, pxylene, naphthalene and 2-methoxynaphthalene, respectively, with methyl acrylate.

In another preferred embodiment of the invention $R_1$ is an alkoxycarbonyl radical, preferably, methoxycarbonyl, $R_2$ is hydrogen and $R_3$ is a carboaryl, preferably, phenyl. Thus for the preparation of an alkyl 3,3-diaryl propanoate, an arene is reacted with an alkyl cinnamate such as methyl or ethyl cinnamate. In one example as shown herein benzene is reacted with methyl cinnamate, thus producing methyl 3,3-diphenyl propanoate.

Oxygen is preferably added to the reaction at 0-10 atmospheres, more preferably 1-2 atmospheres, and the temperature of the reaction is preferably 50-250° C., and more preferably 150-180° C. At temperatures above 250° C., the reaction will still take place, but some amount of decomposition will result. At lower than 50° C., the reaction will still take place, but the turnover will become unproductively small. Similarly, at an $O_2$ pressure above 10 atm, the reaction will still be expected to take place, but the process would not be industrially practical.

The aryl alkenes produced by the process of the invention are useful intermediates particularly for the pharmaceutical industry.

DETAILED DESCRIPTION OF THE INVENTION

The present invention provides a novel oxidative coupling of arenes with olefins, which may optionally use molecular oxygen as the oxidant. Good catalytic activity is exhibited by the Ru compounds $RuCl_3.3H_2O$, $[Ru(CO)_3Cl_2]_2$, $[(\eta^6-C_6H_6)RuCl_2]_2$, $Ru(NO)Cl_3.5H_2O$ and $Ru(F_3CCOCHCOCF_3)_3$ under a pressure of 2 atm of $O_2$ and 6.1 atm of CO at 180° C. In the absence of $O_2$, the alkene itself serves as the oxidant and the coupling is accompanied by a parallel alkene hydrogenation. The reaction is accelerated by electron donating substituents on the arene.

Notably, the dehydrogenative coupling proceeds either under $O_2$ (Equation 1) or in an inert atmosphere (Equation 2). In absence of $O_2$ the olefin itself serves as an oxidant and, for example, when benzene (Ar=phenyl) is reacted with methyl acrylate ($R_1$ is —$COOCH_3$, $R_2$, $R_3$ =H) a 1:1 ratio of cinnamate: propanoate is obtained. In comparison, under 2 atm of $O_2$ the cinnamate yield is doubled and a ratio of about 3:1 of cinnamate: 2-propanoate is obtained (see Table 1). Essentially no organic carbonylation products are observed. The product turnover number increases with CO pressure up to 6.1 atm, beyond which further pressure increase has no beneficial effect. Various arenes and alkenes are reactive (see Table 3). Alky acrylates are by far the most active of the olefins tested.

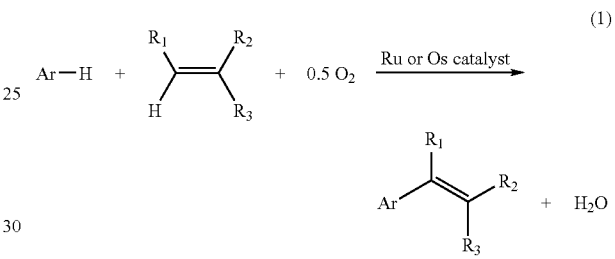

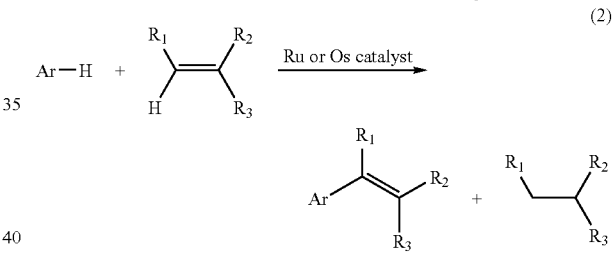

The invention will now be illustrated by the following non-limiting Examples.

EXAMPLE 1

Oxidative Coupling of Benzene with Acrylate Esters

1A. With Ru Complexes as Catalysts

A solution containing 8 ml of benzene, 0.02 mmol of $RuCl_3.3H_2O$ (1) and 5 mmol of methyl or ethyl acrylate in a Fischer-Porter glass reactor was pressurized with 6.1 atm CO and 2 atm $O_2$ and heated to 180° C. with stirring for 48 hours, thus producing methyl or ethyl cinnamate. The results are shown in Table 1.

Addition of a catalytic amount of hydroquinone (HQ) (Entries 6 and 7) or quinone improved the yield, the turnover number and the mass balance of the reaction. Ten or 20 eq of HQ (relative to Ru) had a similar effect. Addition of a radical trap (galvinoxyl) does not retard the reaction and it proceeds as well in the dark (Entry 3 in Table 1).

TABLE 1

Oxidative Coupling of Benzene with Acrylate Esters

| Entry | Conditions[a] | Residual Acrylate % | Yield Pro- panoate % | Yield Cinna- mate % [TON] | Mass Balance % |
|---|---|---|---|---|---|
| 1 | MA*, 2 atm $O_2$ | 22 | 10 | 35 [88] | 67 |
| 2 | MA*, no $O_2$ | 41 | 20 | 20 [50] | 81 |
| 3 | MA*, no $O_2$, no light, 0.2 mmol galvinoxyl | 38 | 23 | 23 [57] | 84 |
| 4 | MA*, 2 atm $O_2$ 5 eq CuO | 23 | 3 | 35 [88] | 63 |
| 5 | EA**, 2 atm $O_2$ | 26 | 10 | 30 [75] | 66 |
| 6 | EA**, 2 atmo $O_2$, 10 eq HQ | 21 | 19 | 40 [100] | 80 |
| 7 | EA**, 2 atm $O_2$, 20 eq HQ | 17 | 21 | 42 [105] | 80 |

[a]Reaction conditions: a solution containing 8 mL of benzene, 0.02 mmol of 1 and 5 mmol of acrylate ester in a Fischer-Porter glass reactor is pressurized with 6.1 atm CO and 2 atm $O_2$ and heated to 180° C. with stirring for 48 hours.
*MA = methyl acrylate.
**EA = ethyl acrylate.
TON = turnover number. Yields are based on acrylate ester.

1B. With $[\eta^6\text{-}C_6H_6\text{—}Ru(H_2O)_3](F_3CSO_3)_2$ as Catalyst with 1 atm of CO A solution containing 8 ml of benzene, 0.02 mmol of $[\eta^6\text{-}C_6H_6\text{—}Ru(H_2O)_3](F_3CSO_3)_2$ and 5 mmol of ethyl acrylate in a Fisher-Porter glass reactor was pressurized with 1 atm CO and 7.1 atm of inert gas (e.g., Argon or $N_2$) and heated to 180° C. with stirring for 48 hours. GC analysis revealed formation of 1.1 mmol (E)-ethyl cinnamate (22% yield, 55 TON) and 1.3 mmol ethyl propanoate (26% yield, 65 TON).

1C. With $Ru(CF_3COCHCOCF_3)_3$ or $OS_3(CO)_{12}$ or $Ru_3(CO)_{12}$ as Catalysts without CO Pressure A solution containing 8 ml of benzene, 0.02 mmol of catalyst (per metal center) and 5 mmol of ethyl acrylate in a Fischer-Porter glass reactor was pressurized with 2 atm of $O_2$ and 6.1 atm of inert gas (e.g., Argon or $N_2$) and heated to 180° C. with stirring for 48 hours. The results are shown in Table 2.

TABLE 2

Oxidative Coupling of Benzene with Acrylate Esters without CO Pressure[a,b]

| Entry | Catalyst | Residual Acrylate % | Yield Pro- panoate % | Yield Cinna- mate % [TON] | Mass Balance % |
|---|---|---|---|---|---|
| 8 | $Ru(CF_3COCHCOCF_3)_3$ | 61 | 4 | 3 [6] | 68 |
| 9 | $Os_3(CO)_{12}$ | 55 | 6 | 3 [6] | 64 |
| 10 | $Ru_3(CO)_{12}$ | 49 | 3 | 2 [4] | 54 |

[a]Reaction conditions: a solution containing 8 mL of benzene, 0.02 mmol of catalyst (per metal center) and 5 mmol of ethyl acrylate in a Fischer-Porter glass reactor is pressurized with 6.1 atm Ar and 2 atm $O_2$ and heated to 180° C. with stirring for 48 hours. Yields are based on ethyl acrylate.
[b]Other catalysts mentioned above gave under this conditions about 1 TON.

1D. With Os Complexes as Catalysts

A solution containing 8 ml of benzene, 0.02 mmol of $OsCl_3 \cdot xH_2O$ (2) or $OsO_4$ (3) and 5 mmol of ethyl acrylate in a Fischer-Porter glass reactor was pressurized under 2 atm of $O_2$ and 6.1 atm of argon and heated to 180° C. with stirring for 48 hours, thus producing ethyl cinnamate. The results are shown in Table 3.

TABLE 3

Oxidative Coupling of Benzene with Ethyl Acrylate Utilizing Os Compounds

| Entry | Conditions[a] | Residual Acrylate % | Yield Pro- panoate % | Yield Cinna- mate % [TON] | Mass Balance % |
|---|---|---|---|---|---|
| 1 | 2, 2 atm $O_2$ and 6.1 atm CO | 26 | 19 | 18 [44] | 63% |
| 2 | 3, 2 atm $O_2$ and 6.1 atm CO | 73 | 6.5 | 6 [15] | 85.5 |

[a]Reaction conditions: a solution containing 8 mL of benzene, 0.02 mmol of 2 or 3 and 5 mmol of ethyl acrylate in a Fischer-Porter glass reactor is pressurized with CO and $O_2$ and heated to 180° C. with stirring for 48 hours. Yields are based on acrylate ester.

EXAMPLE 2

Oxidative Coupling of Various Arenes with Olefins Under $O_2$

In a typical reaction protocol, an 80 mL glass pressure tube is charged with 90 mmol of arene, 0.02 mmol of $RuCl_3 \cdot 3H_2O$, 0.2 mmol HQ and 5 mmol of acrylate. The reactor is then evacuated and then pressurized with 6.1 atm CO and 2 atm $O_2$ and heated to 180° C. with stirring for 48 hours. The liquid phase is sampled and analyzed by gas chromatography, mass spectroscopy and HNMR spectroscopy at the end of the reaction. The products are characterized by comparison with authentic samples. In this way, methyl acrylate was reacted with benzene, chlorobenzene, toluene, anisole, p-xylene, naphthalene and 2-methoxynaphthalene, and ethylene, methyl cinnamate and $H_2C=CH(CF_2)_3CF_3$ were reacted with benzene. The results are shown in Table 4.

TABLE 4

Oxidative Coupling of Various Arenes with Olefins under $O_2^a$

| Entry | Arene | Olefin | Product p:m:o ratio | Yield % [TON] |
|---|---|---|---|---|
| 1 | chlorobenzene | MA | (E)-Methyl 3-(chlorophenyl)propanoate 1:2:0 | 34 [86] |
| 2 | benzene | MA | (E)-Methyl cinnamate | 41 [105] |
| 3 | toluene | MA | (E)-Methyl 3-(tolyl)propanoate 1:1.6:0 | 44 [110] |
| 4 | anisole | MA | (E)-Methyl 3-(methoxyphenyl)propanoate 1:1.3:1.05 | 47 [118] |
| 5 | benzene | Ethylene | Styrene | 3.0 [7.5] |
| 6 | benzene | $H_2C=CH(CF_2)_3CF_3$ | (3,3,4,4,5,5,6,6,6-Nonafluoro-hex-1-enyl) benzene | 4.1 [5.4] |
| 7 | p-xylene | MA | (E)-Methyl 3-(2,5-dimethylphenyl)propanoate | 2.3 [5.7] |
| 8 | p-dichlorobenzene | MA | No coupling product | 0 |
| 9 | naphthalene | MA | (E)-Methyl 3-(2-naphthyl)propanoate | 28 [70] |

[a] The reaction was carried out as described above in Example 2. Entry 5 was carried out under 3.4 atm of CO and 3.4 atm of ethylene. In Entry 6, 2.63 mmol of $H_2C=CH(CF_2)_3CF_3$ were used. (E) is defined according to Stretweiser et al (1972).

The reaction is accelerated by electron donating substituents on the arene.

In summary, a novel Ru- and Os-catalyzed oxidative coupling of arenes with olefins to produce aryl alkenes, which can either directly utilize dioxygen or can utilize the alkene as oxidant and results in reasonable turnover numbers, has been disclosed.

REFERENCES

Asano et al, "Aromatic substitution of olefins. Reaction of ferrocene with styrene in the presence of palladium(II) acetate", *J Chem Commun* 1293 (1970)

Fujiwara et al, "Aromatic substitution of olefins. VI. Arylation of olefins with palladium(II) acetate", *J Am Chem Soc* 91:7166 (1969)

Fujiwara et al, "Aromatic substitution of olefins. XXV. Reactivity of benzene, naphthalene, ferrocene, and furan toward styrene, and the substituent effect on the reaction of monosubstituted benzenes with styrene", *J Org Chem* 41:1681 (1976)

Fujiwara et al, "Exploitation of synthetic reactions via C—H bond activation by transition metal catalysts. Carboxylation and aminomethylation of alkanes or arenes", *Synlett* 591 (1996)

Hong et al, "Rhodium carbonyl-catalyzed activation of carbon-hydrogen bonds for application in organic synthesis. V. Phenylation of olefins with benzenes", *J Mol Catal* 297(1984)

Jia et al, "Efficient activation of aromatic C—H bonds for addition to C—C multiple bonds", *Science* 287:1992 (2000a)

Jia et al, "Novel Pd(II)- and Pt(II)-catalyzed regio- and stereoselective trans-hydroarylation of alkynes by simple arenes", *J Am Chem Soc* 122:7252 (2000b)

Kakiuchi et al, "Ruthenium-catalyzed addition of aromatic imines at the ortho C—H bonds to olefins", *Chem Lett* 111 (1996)

Masato et al, Japanese patent 1193241A2, "Production of Cinnamic Acid Ester Derivative", Aug. 3, 1989

Matsumoto et al, "Anti-Markovnikov Olefin Arylation Catalyzed by an Iridium Complex", *J Am Chem Soc* 122: 7414 (2000a)

Matsumoto et al, "Oxidative arylation of ethylene with benzene to produce styrene" *Chem Lett* 9:1064-1065 (2000b)

Mikami et al, "Catalytic C—H bond activation-asymmetric olefin coupling reaction: the first example of asymmetric Fujiwara-Moritani reaction catalyzed by chiral palladium (II) complexes", *Chem Lett* 55 (1999)

Miura et al, "Palladium-catalyzed oxidative cross-coupling of 2-phenylphenols with alkenes", *Chem Lett* 1103 (1997)

Miura et al, "Oxidative Cross-Coupling of N-(1,1-biphenyl-2yl)benzenesulfonamides or Benzoic and Naphthoic Acids with Alkenes Using a Palladium-Copper Catalyst System under Air", *J Org Chem* 63:5211 (1998)

Moritani et al, "Aromatic substitution of styrene-palladium chloride complex", *Tetrahedron Lett* 1119 (1967)

Moritani et al, U.S. Pat. No. 3,674,884, "Process for the Preparation of Aromatic Hydrocarbons Containing Monoethylenic Unsaturated Radicals", Jul. 4, 1972

Murai et al, "Efficient Catalytic Addition of Aromatic Carbon-Hydrogen Bonds to Olefin" *Nature* 366:529 (1993)

Sasaki et al, "Carbon-carbon double bond insertion in catalytic carbon-hydrogen activation. Dehydrogenative cross-coupling of arenes with olefins", *Chem Lett* 4:685-688 (1988)

Shue R S "Reactions of aromatics and olefins catalyzed by homogeneous palladium(II) compounds under oxygen", *J Catal* 26:112 (1972)

Shue, R S, U.S. Pat. No. 3,855,329, "Olefin Coupling in the Presence of Palladium Carboxylates", Dec. 17, 1974

Stretweiser et al, *Introduction to Organic Chemistry*, 4th. Ed., Prentice-Hall Inc., New Jersey (1992), p. 54

Tanaka et al, Japanese patent 01193241 A2, "Production of Cinnamic Acid Ester Derivative", Aug. 3, 1989

Taube et al, U.S. Pat. No. 6,127,590, "Oxidative Coupling of Olefins and Aromatics Using a Rhodium Catalyst and a Copper(II) Redox Agent", Oct. 3, 2000

Tsuji et al, "Palladium-catalyzed oxidative coupling of aromatic compounds with olefins using tert-butyl perbenzoate as a hydrogen acceptor", *Tetrahedron* 40:2699 (1984)

The invention claimed is:

1. A method for the production of an aryl alkene, comprising reacting an arene with an olefin in the presence of a Ru or Os compound as catalyst, such that an aryl alkene is produced.

2. A method according to claim 1, wherein the reaction is carried out in the presence of molecular oxygen.

3. A method according to claim 2, wherein the reaction is carried out in the presence of a hydroquinone or a quinone.

4. A method according to claim 1, wherein the reaction is carried out in an atmosphere containing CO.

5. A method according to claim 4, wherein the CO atmosphere has a CO pressure of up to about 100 atm.

6. A method according to claim 5, wherein said CO pressure is 6-8 atm.

7. A method according to claim 1, wherein the ruthenium compound is selected from the group consisting of $RuCl_3 \cdot 3H_2O$, $[Ru(CO)_3Cl_2]_2$, $[(\eta^6\text{-}C_6H_6)RuCl_2]_2$, $[(\eta^6\text{-}C_6H_6)\text{—}Ru(H_2O)_3](F_3CSO_3)_2$, $Ru(NO)Cl_3 \cdot 5H_2O$, $Ru(F_3CCOCHCOCF_3)_3$ and $Ru_3(CO)_{12}$.

8. The method according to claim 7, wherein the ruthenium compound is $RuCl_3 \cdot 3H_2O$.

9. A method according claim 1, wherein the osmium compound is selected from the group consisting of $OsCl_3 \cdot xH_2O$, $[Os(CO)_3Cl_2]_2$, $[(\eta^6\text{-}C_6H_6)OsCl_2]_2$, $Os(NO)Cl_3 \cdot 5H_2O$, $Os(F_3CCOCHCOCF_3)_3$ and $OSO_4$.

10. The method according to claim 9, wherein the osmium compound is $OsCl_3 \cdot xH_2O$.

11. A method according to any one of claim 1, for the production of an aryl alkene of the formula:

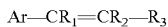

Ar—CR$_1$=CR$_2$—R$_3$ wherein Ar is an aryl radical and R$_1$, R$_2$, R$_3$ independently of each other represent H, alkyl, aryl, alkoxycarbonyl or aryloxycarbonyl.

12. A method according to claim 11, wherein Ar is a carboaryl, or a heteroaryl radical, the aryl radical being optionally substituted by one or more halogen atoms, alkyl optionally substituted by one or more halogen atoms, or alkoxy.

13. A method according to claim 12, wherein said alkyl or alkoxy radical has up to 25 carbon atoms.

14. A method according to any one of claim 1 for the preparation of an alkyl cinnamate which comprises reacting benzene with an alkyl acrylate.

15. A method according to claim 14 for the preparation of methyl cinnamate which comprises reacting benzene with methyl acrylate.

16. A method according to claim 14 for the preparation of ethyl cinnamate which comprises reacting benzene with ethyl acrylate.

17. A method according to any one of claim 1 for the preparation of an alkyl aryl-2-propanoate which comprises reacting an arene with an alkyl acrylate.

18. A method according to claim 17 for the preparation of an alkyl aryl-2-propanoate selected from the group consisting of methyl 3-(chlorophenyl)-2-propanoate, methyl 3-(methoxyphenyl)-2propanoate, methyl 3-(tolyl)-2-propanoate, methyl 3-(2,5-dimethylphenyl)-2-propanoate, methyl 3-(2-naphthyl)-2propanoate and methyl 3-(2- or 6- or 7-methoxy-2-naphthyl)-2propanoate, which comprises reacting an arene selected from the group consisting of chlorobenzene, anisole, toluene, p-xylene, naphthalene and 2-methoxynaphthalene, respectively, with methyl acrylate.

19. A method according to any one of claim 1 for the preparation of styrene which comprises reacting benzene with ethylene.

20. A method according to any one of claim 1 for the preparation of (3,3,4,4,5,5,6,6,6-nonafluoro-hex1-enyl)benzene which comprises reacting benzene with $H_2C$=CH$(CF_2)_3CF_3$.

21. A method in accordance with claim 12, wherein Ar is phenyl or naphthyl.

22. A method in accordance with claim 12, wherein Ar is furyl or thienyl.

23. A method in accordance with claim 13, wherein said alkyl or alkoxy radical has up to 20 carbon atoms.

24. A method in accordance with claim 13, wherein said alkyl or alkoxy radical has up to 10 carbon atoms.

25. A method in accordance with claim 13, wherein said alkyl or alkoxy radical has up to 6 carbon atoms.

* * * * *